United States Patent [19]

Duboff et al.

[11] Patent Number: 5,236,833
[45] Date of Patent: Aug. 17, 1993

[54] DIACETYL PRODUCTION

[75] Inventors: Shirley A. Duboff, Ridgefield; Steven S. Kwon; Dharam V. Vadehra, both of New Milford, all of Conn.

[73] Assignee: Nestec S.A., Vevey, Switzerland

[21] Appl. No.: 852,771

[22] Filed: Mar. 17, 1992

[51] Int. Cl.$^5$ .......................... C12P 7/26; C12R 1/225
[52] U.S. Cl. ....................................... 435/148; 426/50; 426/51; 435/853; 435/856
[58] Field of Search ...................... 435/148, 853, 856; 426/50, 51

[56] References Cited

U.S. PATENT DOCUMENTS

| | | | |
|---|---|---|---|
| 4,200,694 | 4/1980 | Ishii et al. | 426/50 |
| 4,284,651 | 8/1981 | Bruemmer | 426/50 |
| 4,304,862 | 12/1981 | Troller | 435/148 |
| 4,678,673 | 7/1987 | Marshall et al. | 426/46 |
| 4,686,187 | 8/1987 | Sakai et al. | 426/50 |
| 4,867,992 | 9/1989 | Boniello et al. | 426/45 |
| 5,075,226 | 12/1991 | Kaneko et al. | 435/148 |

OTHER PUBLICATIONS

E. B. Collins, "Biosynthesis of Flavor Compounds by Microorganisms", Journal of Dairy Science, vol. 55, No. 7, pp. 1022–1028.

Primary Examiner—Herbert J. Lilling
Attorney, Agent, or Firm—Vogt & O'Donnell

[57] ABSTRACT

A fermented pectin-based substance containing diacetyl is prepared by fermenting an aqueous pectin slurry with a lactic acid-producing bacteria under aerobic conditions. Prior to fermentation, the pectin may be incubated with a pectinase.

20 Claims, No Drawings

DIACETYL PRODUCTION

BACKGROUND OF THE INVENTION

The present invention relates to a process for the production of diacetyl.

Diacetyl is a major constituent of butter flavour, ordinary butter containing about 8-10 ppm. It is also an important flavour compound in dairy products and coffee.

Up to the present time, milk has been used as a source of diacetyl by fermentation which yields about 80 ppm. U.S. Pat. No. 4,678,673 describes the preparation of diacetyl from oilseed products by fermenting with *Lactobacillus casei spp. rhamnosus* AT CC 39595 at a pH of 6 to 7 for less than 8 hours, but the yield of diacetyl is never more than 44 ppm. U.S. Pat. No. 4,867,992 describes the preparation of a buttery flavour containing diacetyl by fermenting a coffee substrate with a lactic acid producing bacteria.

SUMMARY OF THE INVENTION

We have found, surprisingly, that by fermenting a pectin substrate with a strain of lactic acid producing bacteria, we can obtain yields of diacetyl of above 500 ppm.

Accordingly, the present invention provides a process for the preparation of a fermented pectin-based substance containing diacetyl which comprises fermenting an aqueous pectin slurry with a lactic acid producing bacteria at a temperature from 16° C. to 38° C. and a pH of 4.0 to 7.0 for a period of 8 to 24 hours under aerobic conditions. Advantageously, before fermentation, the pectin to be fermented is incubated with pectinase.

DETAILED DESCRIPTION OF THE INVENTION

In the practice of the present invention, a pectin slurry may be prepared, preferably, from distilled water or from deionized water. The concentration of the pectin in the slurry may be from 5 to 50%, preferably from 10 to 40%, and especially from 15 to 30% by weight.

The pectin in the slurry may be a mixture of pectins and may be a citrus pectin or an apple pectin.

The fermentation media may be prepared by adding sodium chloride to the pectin slurry, and the alkaline salts of pyruvic and citric acid, preferably the sodium salts. The amount of sodium chloride may be from 0.25 to 2.5%, and preferably from 0.5 to 1.5%, by weight based on the weight of the slurry. The amount of pyruvate may be from 0.25 to 2.5%, and preferably from 0.5 to 1.25%, by weight based on the weight of the slurry. The amount of citrate may be from 0.5 to 5%, and preferably from 1.5 to 3.5%, by weight based on the weight of the slurry. The fermentation media may then conveniently be autoclaved, for example from 100° to 120° C. over 5 to 30 minutes.

The lactic acid producing bacteria may be one known to be capable of producing diacetyl, e.g., *Leuconostoc cremoris, Streptococcus lactis* subspecies *diacetylactis*, but conveniently, the lactic acid producing bacteria is *Lactobacillus casei* (hereinafter referred to as *L.casei*). Examples of suitable strains are *L.casei* ATCC (American Type Culture Collection) 334 isolated from Emmental cheese, *L.casei* ATCC 11582 - lactose negative and *L.casei* subspecies *tolerans* ATCC 25599 isolated from milk.

The concentration range of *L. casei* is conveniently from $5 \times 10^5$ to $1 \times 10^9$ cells and preferably from $5 \times 10^6$ to $1 \times 10^8$ cells per milliliter of the slurry.

The fermentation temperature is preferably from 30° to 35° C. The pH during the fermentation is preferably from 5 to 5.75. The duration of the fermentation is preferably from 12 to 20 hours. Aerobic conditions may be achieved by aeration, such as by bubbling in air or oxygen in the aqueous pectin slurry and agitating the slurry, conveniently with stirring at 100 to 300 RPM, preferably from 225 to 275 RPM.

When the aqueous pectin slurry is first treated with pectinase, the fermented slurry was pasteurised and the resultant product was found to contain 1700 ppm of diacetyl.

The amount of pectinase may be from 0.1 to 10%, preferably from 0.2 to 5% and especially from 0.5 to 2.5%, by weight based on the weight of the pectin slurry. The incubation temperature may be from 35° to 55° C. and preferably from 40° to 50° C. The duration of the incubation may be from 30 minutes to 6 hours, preferably from 1 to 3 hours. Advantageously, the incubation mixture is agitated, for example by stirring at 100 to 500 RPM, preferably from 200 to 300 RPM.

After incubation with pectinase, large precipitates are preferably removed, for example, by filtration. Afterwards, the pectinase treated mixture may be autoclaved, for example, from 100°-120° C. over 5 to 30 minutes, or it may be used directly to prepare the media for fermentation with the lactic acid producing bacteria as hereinbefore described followed by autoclaving.

EXAMPLES

The following example further illustrates the present invention. Parts and percentages indicated are by weight.

EXAMPLE 10 parts of apple pectin and 10 parts of lemon pectin together with 80 parts of distilled deionised water were treated with 1 part of pectinase by incubating at 40° C. for 2 hours with stirring at 250 RPM.

To the above pectinase treated pectin slurry were added 0.85% NaCl, 0.75% sodium pyruvate and 2.5% sodium citrate and the final media autoclaved at 110° C. for 15 minutes.

*L. casei* ATCC=334 was added at a concentration range of $1 \times 10^7$ cells per milliliter of the slurry and fermentation took place at 32° C.; pH 5.5 over 18 hours with stirring at 250 RPM.

We claim:

1. A process for preparation of a fermented pectin-based substance containing diacetyl comprising incubating an aqueous slurry of pectin with a pectinase to obtain a pectinase-treated pectin substance and then fermenting an aqueous slurry of the pectinase-treated pectin substance with a lactic acid-producing bacteria at a temperature of from 16° C. to 38° C. and at a pH of from 4 to 7 for a period of from 8 hours to 24 hours under aerobic conditions to obtain a fermented pectin-based substance containing diacetyl.

2. A process according to claim 1 wherein the aqueous slurry of the pectinase-treated pectin substance which is fermented contains an alkaline salt of pyruvic acid.

3. A process according to claim 2 wherein the aqueous slurry of the pectinase-treated pectin substance which is fermented contains sodium chloride.

4. A process according to claim 3 wherein the aqueous slurry of the pectinase-treated pectin substance which is fermented contains an alkaline salt of citric acid.

5. A process according to claim 1 further comprising pasteurizing the fermented pectin-based substance containing diacetyl.

6. A process according to claim 4 further comprising pasteurizing the fermented pectin-based substance containing diacetyl.

7. A process according to claim 1 wherein the bacteria are selected from the group consisting of *Lactobacillus casei, Leuconostoc cermoris* and *streptococcus lactic diacetylactics*.

8. A process according to claim 1 wherein the bacteria are *Lactobacillus casei*.

9. A process according to claim 3 wherein the *Lactobacillus casei* are selected from the group of strains consisting of *L. casei* ATCC 334, ATCC 11582 and ATCC25599.

10. A process according to claim 1 wherein the pH is from 5 to 5.75.

11. A process according to claim 8 wherein the pH is from 5 to 5.75.

12. A process according to claim 1 further comprising treating the fermented pectin-based substance containing diacetyl at a temperature of from 100° C. to 120° C. from 5 minutes to 30 minutes.

13. A process according to claim 12 further comprising treating the pectinase-treated pectin substance at a temperature of from 100° C. to 120° C. for a period of from 5 minutes to 30 minutes to obtain a heat-treated substance and then fermenting the aqueous slurry of the heat-treated pectin substance.

14. A process according to claim 1 wherein the pectin is selected from the group of pectins consisting of citrus pectin and apple pectin.

15. A process for preparation of a fermented pectin-based substance containing diacetyl comprising fermented a pectinase-treated pectin in an aqueous slurry with a lactic acid-producing bacteria at a temperature of from 16° C. to 38° C. and at a pH of from 4 to 7 for a period of from 8 hours to 24 hours under aerobic conditions to obtain a fermented pectin-based substance containing diacetyl.

16. A process according to claim 15 wherein the aqueous slurry contains sodium chloride and alkaline salts of pyruvic acid and citric acid.

17. A process according to claim 16 wherein the bacteria is *Lactobacillus casei*.

18. A process according to claim 17 wherein the *Lactobacillus casei* are selected from the group of strains consisting of *L. casei* ATCC 334, ATCC 11582 and ATCC 25599.

19. A process according to claim 17 wherein the pH is from 5 to 5.75.

20. A process according to claim 15 further comprising pasteurizing the fermented pectin-based substance containing diacetyl.

* * * * *

UNITED STATES PATENT AND TRADEMARK OFFICE
CERTIFICATE OF CORRECTION

PATENT NO.  : 5,236,833
DATED       : August 17, 1993
INVENTOR(S) : Shirley A. Duboff, et al.

It is certified that error appears in the above-identified patent and that said Letters Patent is hereby corrected as shown below:

Column 3, line 16, (line 3 of claim 7), "cermoris" should be --cremoris--.

Column 3, line 31 (line 4 of claim 12), insert --for-- before "from".

Column 4, lines 11-12 (lines 2-3 of claim 15), "fermented" should be --fermenting--.

Signed and Sealed this

Twenty-second Day of March, 1994

Attest:

BRUCE LEHMAN

*Attesting Officer*   *Commissioner of Patents and Trademarks*